United States Patent [19]

Ales et al.

[11] Patent Number: 4,639,949
[45] Date of Patent: Feb. 3, 1987

[54] ELASTIC FORM-FITTING CLOSURE CONSTRUCTIONS FOR DISPOSABLE GARMENTS

[75] Inventors: Thomas M. Ales, Winnebago County; David T. Strohbeen, Outagamie County; Joyce A. Damico, Winnebago County; Paul T. Van Gompel; Kent W. Abel, both of Outagamie County, all of Wis.

[73] Assignee: Kimberly-Clark Corporation, Neenah, Wis.

[21] Appl. No.: 690,348

[22] Filed: Jan. 10, 1985

[51] Int. Cl.$^4$ .................... A41B 9/00; A61F 13/16
[52] U.S. Cl. ................................. 2/400; 2/402; 604/385 A
[58] Field of Search ............ 2/400, 401, 402, 403, 2/221; 604/385.2, 392, 378, 391, 358, 396

[56] References Cited

U.S. PATENT DOCUMENTS

| | | | |
|---|---|---|---|
| 3,560,292 | 2/1971 | Butter | 2/402 X |
| 3,828,784 | 8/1974 | Zoephel | 604/385.2 |
| 4,336,803 | 6/1982 | Repke | 604/385.2 |
| 4,407,284 | 10/1983 | Pieniak | 604/385.2 |
| 4,437,860 | 3/1984 | Sigl et al. | 604/385.2 |
| 4,547,243 | 10/1985 | Brody | 604/385.2 |
| 4,556,596 | 12/1985 | Meuli | 604/385.2 |

Primary Examiner—Werner H. Schroeder
Assistant Examiner—J. L. Olds
Attorney, Agent, or Firm—Douglas L. Miller; Donald L. Traut; Jeremiah J. Duggan

[57] ABSTRACT

Disposable garments (10) having an elasticized opening including an elastic element (25, 60, 70) joined to a marginal portion of an exterior panel (21, 40, 61, 71) of the garment about the opening along a plurality of spaced bond points (50), and also joined to a marginal portion of an interior panel (20, 62, 72) or folded-over portion of the exterior panel (40a) along the opening, with the outer edges of the elastic element and panel portions joined thereto being substantially coincident. The elastic element is joined to the panel portions in an elongated condition and thereafter allowed to retract to produce micro-buckling (51) of the exterior panel between the bond points.

12 Claims, 27 Drawing Figures

ELASTIC FORM-FITTING CLOSURE CONSTRUCTIONS FOR DISPOSABLE GARMENTS

TECHNICAL FIELD

This invention relates generally to the field of disposable garments; more specifically, this invention relates to elastic constructions which may be used along openings of disposable garments to provide a form-fitting closure, such as along a person's waist, leg, ankle, neck or wrist.

BACKGROUND ART

The term "disposable garments" as used herein refers to those types of articles intended to be worn by persons, including infants and adults, which are designed for single use or temporary use and are meant to be disposed of after being used once instead of being laundered or dry cleaned for re-use. Some examples of disposable garments within this general type are disposable diapers; adult incontinence garments; hospital garments such as surgical gowns, caps and booties or shoe covers; single use garments intended to be worn by patients in a hospital such as disposable pajamas and gowns; and various other types of garments, such as laboratory coats, disposable shower caps, etc. Single use or disposable garments are most usually made of lightweight film or sheet material such as thermoplastic films, nonwoven sheets of thermoplastic or cellulosic fibers, papers, coated films or papers and various composites of one or more of these types of materials. The materials used for disposable garments are distinguishable from textiles that are used to make a sewn garment or article intended for long term use and subject to repeated laundering or drycleaning. Further, disposable garments must generally be manufactured using techniques such as die-cutting, heat sealing, sonic sealing, adhesive bonding, etc., instead of the sewing methods customarily employed to produce textile garments.

Many disposable garments employ some form of elasticized body-encircling opening in order to provide a form-fitting closure with part of a person's body. For example, a disposable diaper will often have elasticized leg openings in order to reduce leakage around an infant's legs, or sometimes an elasticized waist opening; a gown or coat-like disposable garment will often have elasticized wrist openings to provide a snug fit about a person's wrists; disposable booties or shoe covers may have an elasticized ankle encircling portion; and a disposable cap may have an elasticized opening to fit about a person's head.

The prior art techniques of which we are aware most generally used to provide elasticized openings for disposable garments are typified by patents relating to disposable diapers, particularly U.S. Pat. Nos. 3,860,003 (Buell), 4,050,462 (Woon et al., assigned to the assignee of this application), and 4,325,372 (Teed). The disposable diapers of these patents are three-layer composite structures comprising a liquid permeable bodyside liner, a liquid impermeable outer cover and an absorbent batt sandwiched between the liner and the cover. In order to provide elasticized leg openings, a strip of elastomeric material is included in the garments along the portions thereof which define the leg openings. The manner in which the elastomeric strips are incorporated in these garments involves joining the elastomeric strip to one layer of the garment, either the liner or the cover, intermittently bonding portions of one surface of the elastomeric strip to one layer or the other, and spacing the elastomeric strip from the edge of the garment at the leg openings. The techniques of forming elasticized openings in disposable garments disclosed in these patents are also typical of other prior art constructions. These techniques result in a disposable diaper having elasticized leg openings that have a ruffled or gathered appearance. This style of elasticized leg opening, while acceptable for disposable diapers, would be unacceptable or undesirable for various other types of disposable garments; also, elasticized leg openings for disposable diapers having a different appearance than the typical prior art constructions would be advantageous.

We have therefore developed the elasticized form-fitting closures of this invention for use with disposable garments to provide a tailored look to the garments instead of the ruffled or gathered opening typical of prior constructions. This allows the production of disposable garments that have more attractive looking elasticized openings. The construction of the present invention can be employed with disposable diapers for example, but it is also suitable for other types of disposable garments such as panties, gowns, booties, shoe covers and the like, and results in a more presentable appearance that may enhance or increase the use of disposable garments.

SUMMARY OF THE INVENTION

Our present invention provides an elastic construction suitable for forming one or more elasticized openings in a disposable garment according to which (1) an elastic element is joined to marginal portions of both inner and outer layers of a disposable garment around an opening, or to a layer folded over opposed surfaces of the elastic element in the case of a disposable garment having a single layer along an opening, (2) the outer edge of the elastic element is coincident or substantially coincident with the outer edges of each garment layer to which it is joined, and (3) the portion of the outer layer along the elastic element and the surface of the elastic element contacting such portion are joined together along a plurality of spaced bond points area such that the elastic element causes micro-buckling of the outer layer between the bond points when in a retracted condition. This combination of features results in disposable garments having elasticized openings that closely resemble the appearance of a sewn cloth garment, as well as other advantages, as will be explained in detail hereinafter.

DESCRIPTION OF THE DRAWINGS

The present invention is described below with reference to the following drawings, in which.

BEST MODES FOR CARRYING OUT THE INVENTION

(a) FIGS. 1–10

Figures 1, 2, 3:
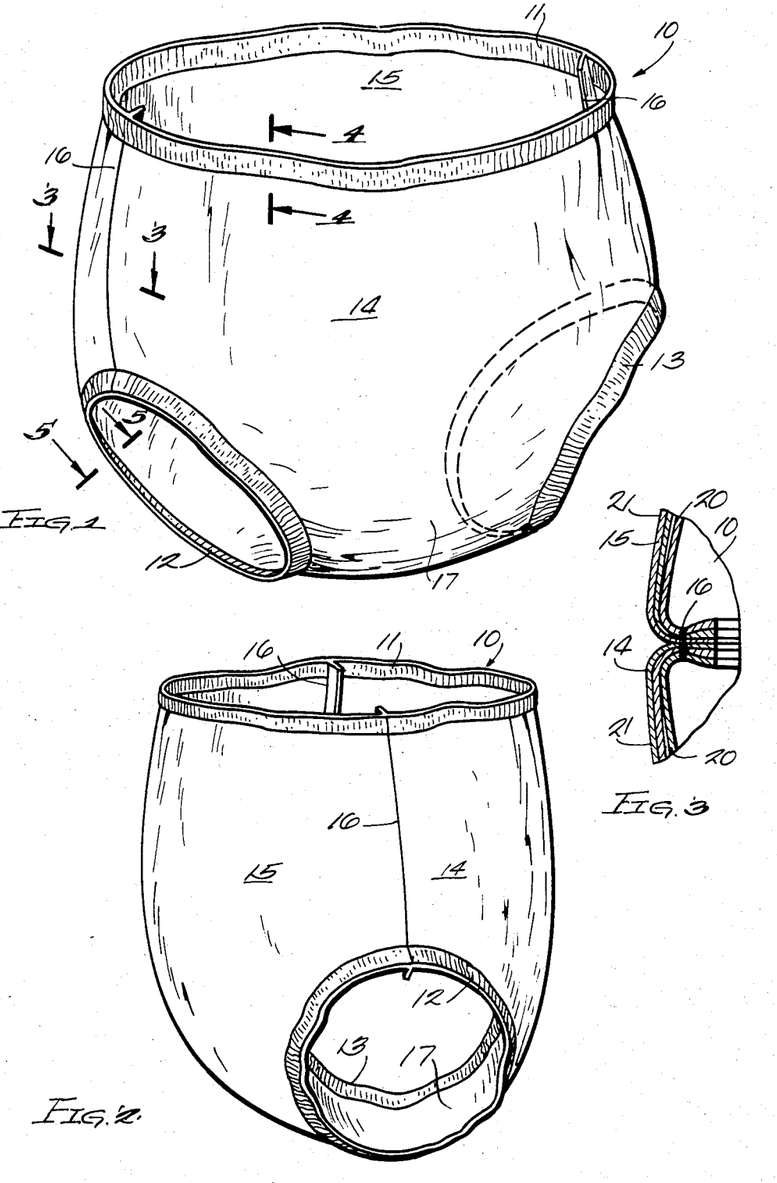
FIG. 1 is a front perspective view of a disposable panty incorporating elasticized leg and waist openings according to the present invention.
FIG. 2 is a side perspective view of the disposable panty of FIG. 1.
FIG. 3 is a sectional view of the side seam construction of the panty of FIG. 1.

FIGS. 1 and 2 illustrate, in front and side perspective views respectively, a disposable panty 10 including an elasticized waist band 11 and elasticized leg bands 12 and 13 constructed in accordance with the present invention. The panty 10 has a front panel 14 and rear panel 15 joined together along side seams 16 to form a completed garment. The panty 10 can be made, for example, from a single flat blank cut to the appropriate configuration and folded along crotch portion 17 between the leg openings or from separate front and rear panels seamed together along the crotch portion.

The front panel 14 and rear panel 15 of the panty are of the same construction and each includes (referring now to FIGS. 4 and 5) a bodyside liner 20 and an outer cover 21. An absorbent batt 22 is positioned between the liner 20 and cover 21 and may be secured to either the liner or the cover, or both, by any suitable means well known in the art such as lines or dots of adhesive, pressure sensitive tapes, sonic seals, heat seals, etc., or the batt may be enclosed by but not secured to the liner or the cover.

As shown in FIG. 3, the side seams 16 are formed by seaming together contacting portions of the outer cover 21 by any suitable means well known in the art, such as sonic sealing, adhesive bonding, heat sealing, adhesive coated tapes, etc. This leaves a narrow fin inside the garment, which can be made relatively narrow such as about 1/16 to ⅛ inch wide so as to minimize the amount of the seam located along the interior of the garment. Any suitable side seam construction can be used in a disposable garment including an elasticized portion according to the present invention.

Figure 4:
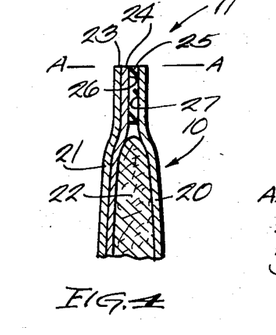
FIG. 4 is a sectional view of the elasticized waist band of the panty of FIG. 1.
Figure 5:
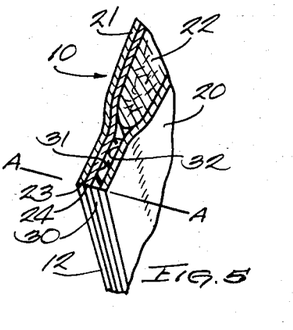
FIG. 5 is a sectional view of an elasticized leg band of the panty of FIG. 1.

The present invention is concerned with the construction of elasticized openings in a disposable garment such as at the waist and legs of the disposable panty 10. The sectional view of FIG. 4 illustrates the construction along the waist band 11 of the panty 10, and the sectional view of FIG. 5 illustrates the construction along the leg bands 12 and 13. As illustrated in these two drawings, the outer cover 21 of the panty is a two-layer sheet material having an outer layer 23 of fibrous nonwoven material and an inner layer 24 of plastic material; this is a particularly-preferred material for use with the elastic construction of the present invention in a disposable panty and is more fully described in the co-pending application of William M. Heran et al entitled Disposable Underpants, such as Infant's Training Pants and the Like filed on the same date herewith, U.S. Ser. No. 690,351, and assigned to the assignee of this application.

As shown in FIG. 4, an elastic element 25 is joined along its first or exterior surface 26 to a marginal portion of layer 24 of the outer cover 21 of the disposable panty 10 and joined along its opposite second or inner surface 27 to a marginal portion of the bodyside liner 20 of the garment. Referring back to FIGS. 1 and 2, the elastic element 25 extends entirely around the waist band 11 of the panty 10; thus, there will be a portion of elastic element 25 joined as shown in FIG. 4 to the marginal portion of the front panel 14 which extends about part of the waist band 11 and another portion of the elastic element 25 joined to a marginal portion of the rear panel 15 of the panty which extends about the balance of the waist band 11. Similarly, referring now to FIG. 5, an elastic element 30 extends about the circumference of the leg opening 12 and has its first or exterior surface 31 joined to the inner layer 24 of a marginal portion of the outer cover 21 about the leg opening and its second or inner surface 32 joined to a marginal portion of the bodyside liner 20 about a leg opening. A similar elastic element extends about the leg opening 13 in the same manner. Referring again to FIGS. 1 and 2, an elastic element 30 extends about the circumference of each leg band 12 and 13.

FIGS. 4 and 5 illustrate a first essential characteristic of the present invention according to which the elastic element 25 is joined to both the bodyside liner 20 and outer cover 21 of the disposable panty about the waist band 11; similarly, the elastic element 30 is joined to both the liner 20 and outer cover 21 of the panty about each of the leg openings 12 and 13.

FIGS. 4 and 5 further illustrate a second essential characteristic of the present invention according to which the outer edge of the elastic element 25 is coincident with the outer edges of the bodyside liner 20 and outer cover 21, which relationship is denoted by the line A—A in FIG. 4. Similarly, the outer edge of the elastic element 30 is coincident with the outer edges of the bodyside liner and outer cover 21 about each of the leg openings 12 and 13, which relationship is indicated by the line A—A in FIG. 5. Thus, the outermost edge of neither the liner 20 or cover 21 extends beyond the outermost edge of the elastic element along the waist band or the leg bands of the disposable panty 10. The outer edges of these several elements can be made coincident during manufacture of the garment by simultaneously cutting through the outer cover, elastic element and bodyside liner or by appropriately registering cutting of the outer cover and liner relative to the outer edge of the elastic element.

Figure 6:
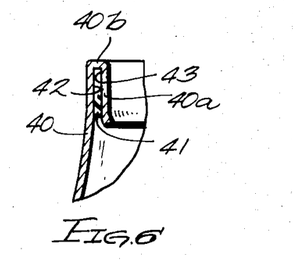
FIG. 6 is a sectional view of an elasticized opening of an alternate construction of a disposable garment.

The sectional view of FIG. 6 illustrates an alternate construction for a disposable garment incorporating the above two features of the present invention in a disposable garment which has a single layer 40 at an opening that is elasticized. In this version, an elastic element 41 has its first or exterior surface 42 joined to the layer 40 about the opening. The layer 40 is folded over the elastic element 41 and the second or inner surface 43 of the elastic element is joined to the folded-over portion 40a of the layer 40. This drawing illustrates an alternate form of the first essential characteristic of this invention, in that the elastic element 41 is joined to a layer of garment material along both of its surfaces 42 and 43, with the layer on one side of the elastic element comprising a folded-over portion of the same layer that is joined to the other surface of the elastic element. As to the second characteristic, the outer edge of the elastic element 41 is not strictly coincident with the outermost edge of the layer 40 since the bight portion 40b thereof is folded about the outer edge of the elastic element 41. The bight portion 40b of the layer 40 is to be adjacent the outer edge of the elastic element of 41. Thus, for the purposes of the present invention, and as used in the claims, the term "substantially coincident" wth respect to the outer edges of an elastic element and the layer or layers of the garment to which it is joined is defined to include structures as illustrated in FIGS. 4 and 5 in which the edges of the layers of the garment and the elastic element are exactly coincident and also the structure as illustrated in FIG. 6 in which the difference between the outer edge of the elastic element and a folded layer to which it is joined differ by no more than the thickness of the layer to which the elastic element is joined. The outer edges of these several elements can be made substantially coincident when a garment is manufactured by folding as described or by appropriately registering the cutting of an outer cover and a liner relative to the outer edge of an elastic element. The folded edge construction as shown in FIG. 6 is suitable for disposable garments such as gowns, caps, booties and the like that do not require inner and outer layers as in the panty 10.

FIGS. 7-10 illustrate a third essential characteristic of the present invention. These drawings illustrate the elastic element 25 encircling the waist opening of the garment as shown in FIG. 1, it being understood that the joinder of the elastic elements 30 and 41 in FIGS. 5 and 6 will be the same so that the ensuing description is also applicable to these drawings.

Figures 7, 8, 9, 10:
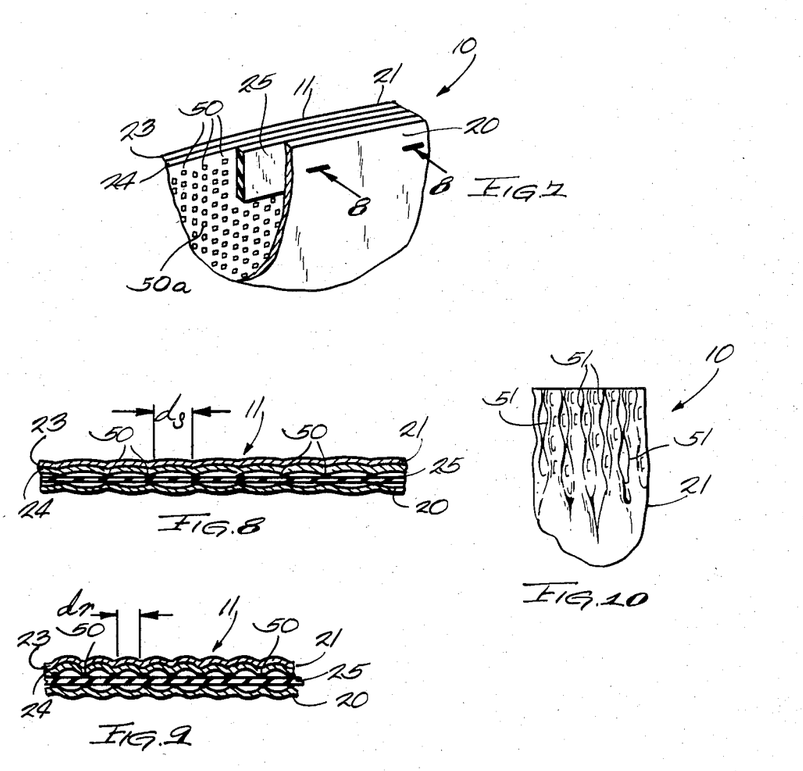
FIG. 7 is a perspective view of a marginal portion of the disposable panty of FIG. 1.
FIG. 8 is a sectional view illustrating the joinder of the elastic element to the disposable garment of FIG. 1 during the manufacture of the garment when the elastic element is in an extended condition.
FIG. 9 is a sectional view along the same plane as FIG. 8 illustrating the elastic element in its retracted condition in the finished garment.
FIG. 10 is a front perspective view of an exterior portion of the disposable panty of FIG. 1 depicting an elasticized opening when the elastic element is in its retracted condition.

Considering FIG. 7 first, the marginal portion of the outer cover 21 of the panty 10 to which the elastic element 25 is joined includes a plurality of closely-spaced bond points 50 extending about the entire circumference of the waistband 11 of the garment. As explained in detail below, the bond points 50 may comprise fused areas or embossments in the material of which the outer cover 21 is made; the bond points typically extend along the entire surface of the sheet from which the layer is made as suggested by the group of bond points 50a in FIG. 7, but it is essential that the bond points 50 be formed at least along the marginal portion of the layer to which the elastic element 25 is joined. The elastic element 25 is joined to the garment when in an extended or stretched during manufacture of the panty 10, illustrated in the sectional view of FIG. 8. As shown in FIG. 8, each bond point 50 is spaced from its neighboring bond points in the direction of elongation of the elastic element by a discrete distance $d_s$. Neighboring bond points also are spaced from each other in the direction transverse to the direction of elongation of the elastic element. The elastic element 25 is joined to the bond points 50, and may or may not also be joined to the material of the outer cover 21 between the bond points when first attached thereto in a stretched condition during part of the manufacturing process. After manufacture of the panty 10 is completed, however, the elastic element 25 is allowed to retract, which condition is illustrated in cross section in FIG. 9. When the elastic element 25 has retracted, it remains joined to the bond points 50 of the outer cover but it is not joined to the intervening sections of the outer cover between the bond points. The retraction of the elastic element 25 while remaining joined along to the bond points brings the bond points closer together, shown as distance $d_r$ in FIG. 9, the distance $d_r$ being less than $d_s$. This results in a micro-buckling or micro-ribbing of the outer cover 21 between the bond points, which condition is depicted in FIG. 9 by the curved sections or micro-ribbing 51 of the outer cover between the bond points. FIG. 10 shows the exterior of the panty 10 along the waist band area to further illustrate the nature of its construction when the elastic element 25 is retracted. Very fine micro-buckling or micro-ribbing 51 of the outer cover 21 is illustrated in FIG. 10 which extends transversely of the elastic element 25.

(b) FIGS. 11-14a

The photomicrographs of FIGS. 11-14a provide further elucidation of the joinder of an elastic element to a disposable garment in accordance with this invention.

Figure 11:
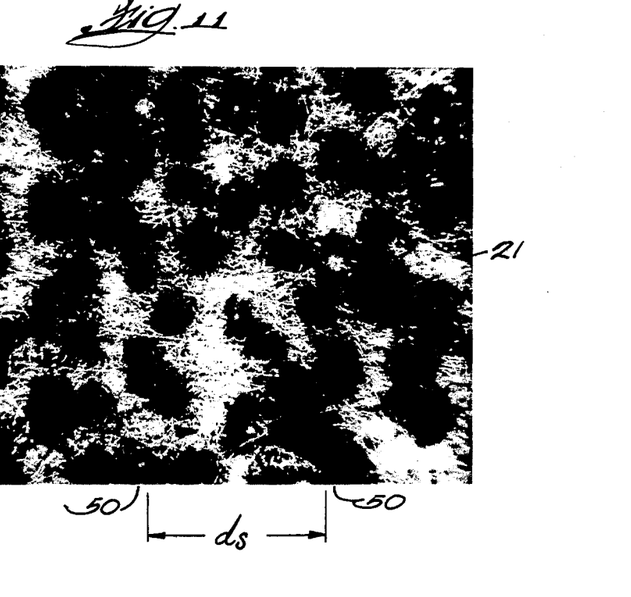
FIG. 11 is a photomicrograph at 13.2× of one type of material suitable for use in a disposable garment in the practice of this invention, shown in plan view.

FIG. 11 is a 13.2× enlargement of a portion of material for the outer cover 21 which, as previously described is a two-layer composite structure consisting of an outer layer 23 of non-woven fibrous material and an inner layer 24 of plastic extrusion coated onto the fibrous outer layer 23. The nonwoven fibrous outer layer 23 was thermally bonded together and the fibers thereof fused to one another to produce a series of bond points 50. The bond points 50 are smooth glass-like fused zones of the layer 23, whereas the remaining material of the layer between the bond points is relatively rough or fibrous in surface texture. Further, the bond points 50 are stiff or rigid, whereas the remaining material between the bond points is flexible. When the inner layer 24 of plastic material is extrusion coated onto the outer layer 23, the plastic material in molten form develops high adhesion to the bond points, and also adheres to the fibrous material between the bond points but usually at a lesser degree of adhesion, thereby resulting in an embossed composite web. The bond points are illustrated in FIG. 11 as being rectangular in shape, but they may have other configurations such as circular, triangular, hexagonal, etc. The distance between neighboring bond points 50 in the direction of elongation of an elastic element, generally circumferential relative to the opening which is to be elasticized, is identified as $d_s$ in FIG. 11. It will be noted that the bond points 50 of FIG. 11 are arranged in alternating staggered rows, but again, other lineal arrangements of the bond points may be employed.

Figure 12:
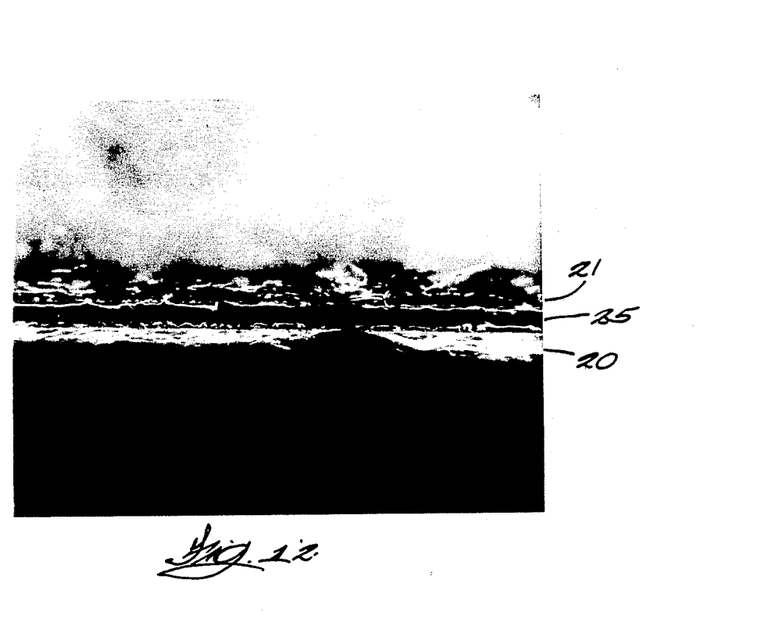
FIG. 12 is a photomicrograph at 13.2× of the material of FIG. 11 in cross-section with an elastic element joined thereto in accordance with the present invention, shown in its extended condition.

The photomicrograph of FIG. 12 illustrates the material of FIG. 11 in cross-section when an elastic element 25 is joined thereto in a stretched condition. Again, the distance between bond points 50 is shown as $d_s$ in this photomicrograph. This photomicrograph represents an intermediate step in the manufacture of a disposable garment such as the panty 10 during which the elastic element is joined to the outer cover 21 and the liner 20 while in a stretched or elongated condition. In connection with the specific materials illustrated in FIG. 12, the elastic element 25 was stretched to an elongation of 50% when joined to the cover 21 and liner 20 in the manner illustrated.

Figure 13:
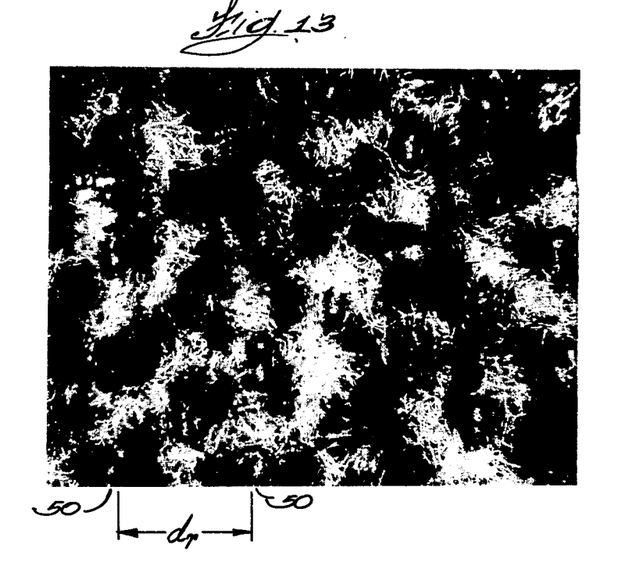
FIG. 13 is a photomicrograph plan view at 13.2× of the structure illustrated in FIG. 12 with the elastic element in its retracted condition.

The photomicrograph of FIG. 13 illustrates the material of FIG. 12 after the elastic element 25 has been allowed to retract and is a plan view similar to that of FIG. 11. As is evident from this photomicrograph, the bond points 50 have been drawn closer together due to the retraction of the elastic element 25. The photomicrograph of FIG. 13 is at the same degree of magnification, 13.2×, as the photomicrograph of FIG. 11, and it can be seen that the distance $d_r$ between the bond points after retraction of the elastic element is less than the distance $d_s$ between the bond points at the time the elastic element is initially joined to the layer 21 and liner 20.

Figure 14:
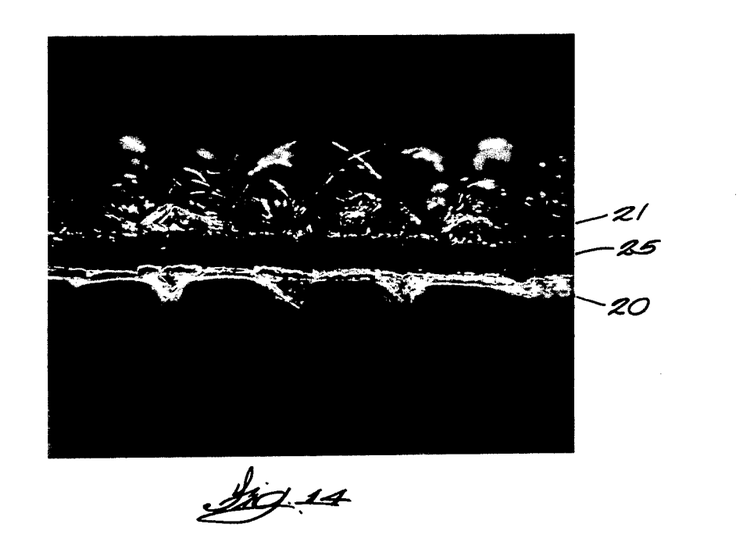
FIG. 14 is a photomicrograph at 13.2× of the structure of FIG. 13 illustrated in cross-section.
Figure 14A:
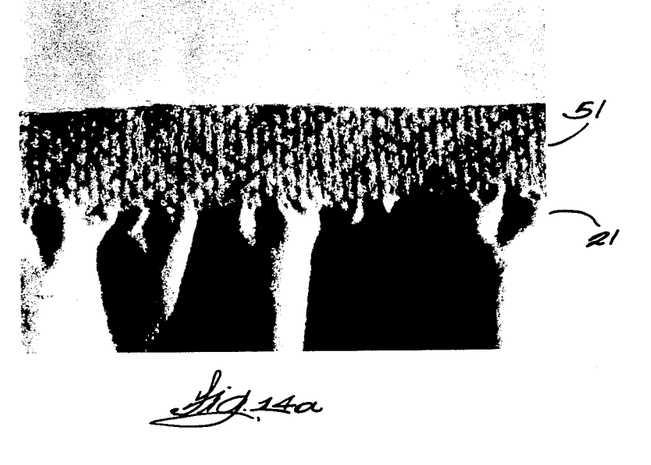
FIG. 14a is a photomicrograph at 2× illustrating the front view of the structure of FIGS. 13 and 14.

The photomicrograph of FIG. 14 illustrates the material of FIG. 13 in cross-section. Again, it will be noted that the bond points 50 are closer to each other following retraction of the elastic element. Most clearly shown in this figure, however, is the micro-buckling or micro-ribbing of the outer layer 21 due to the retraction of elastic element 25. This results in the outer cover 21 having very fine striations or ribbing 51 in a direction transverse to the direction of retraction (and elongation) of the elastic element, best illustrated in FIG. 14a which is a photomicrograph front view at 2× of the material of FIGS. 13 and 14. During retraction of the elastic element to the condition illustrated in FIGS. 13-14a, the elastic element remains joined to the bond points 50 because of their smooth glass-like rigid structure, but the elastic element becomes disengaged from material of the outer cover between the bond points to which it may have been joined during the initial condition shown in FIG. 12; this is because the adhesion of the elastic element to the smooth rigid bond points is significantly higher than its adhesion to the rough flexible material between the bond points.

(c) FIGS. 15-22

The following presents an explanation of the mechanism we believe provides the foregoing finely ribbed-like elasticized band for a disposable garment.

Figure 15:
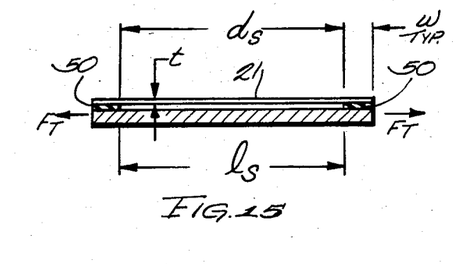
FIGS. 15, 15a, 16, 17, 18, 18a, 19, 20, 21 and 22 are schematic diagrams of various sections of a disposable garment as referred to in part (c) of the following description which illustrate the mechanism of the present invention.

There are essentially three phases to the mechanism as depicted in FIGS. 15-22, which are shown two dimensionally bearing in mind that the mechanism occurs across the depth of the bond between the elastic element and outer cover bond in a similar manner. With respect to the elements identified in FIG. 15:

w = width of the bond points 50;
$d_s$ = length of outer cover 21 between bond points when elastic element 25 is attached in stretched condition;
$l_s$ = length of stretched elastic element;
$d_r$ = length of outer cover when elastic element is contracted;
$l_r$ = length of elastic element when retracted;
$F_T$ = force required to hold elastic element in position $l_s$; and
t = thickness of outer cover.

In phase 1, illustrated in FIG. 15, the attachment phase, the elastic element is stretched and attached to the outer cover material (which is effectively in an unstretched state). In phase 2, illustrated in FIG. 16, the buckling failure phase, the elastic element is allowed to contract which places a compressive load on the outer cover material until it reaches its load carrying limit and fails by buckling. In phase 3, FIG. 17, the retracted phase, the portion of the elastic element between the bond points returns to its original unstretched length while the outer cover material effectively remains the same length but is in a buckled condition between the bond points.

Figure 15A:
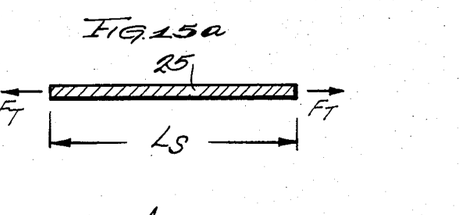
Figure 16:
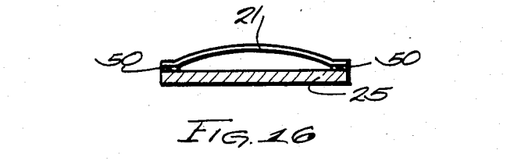

In the first phase, FIG. 15, the elastic element is elongated by the application of an external force and joined to the bond points 50 of the outer cover during the manufacture of a garment. FIG. 15a is a free body diagram illustrating the force applied to the elastic element to stretch it to length "$L_s$", at which length the elastic element is joined to the bond points. The force required to hold an elastic element at a stretched length "$L_s$" can be determined as a function of its stretched length minus its retracted length "$L_r$". This relationship for linear springs is Hooke's Law:

$$F = K(L_2 - L_1) \tag{Eq. 1}$$

With reference to FIG. 15a:

$$F_T = K_E(L_s - L_r) \tag{Eq. 2}$$

Where "$K_E$" is the slope of the line between the displacement ($L_s - L_r$) and "$F_T$" the force developed upon stretching the elastic element from retracted length "$L_r$" to stretched length "$L_s$". The elastic element may not behave as a linear spring but the force can be determined empirically as a function "$K_E$" of the displacement. "$K_E$" will represent the spring constant for the elastic element, which is assumed to generally remain constant as the change in length of the elastic element increases. At any stretched length "l" of the elastic element, the force "$F_E$" in the elastic element is:

$$F_E = K_E(l - l_r) \tag{Eq. 3}$$

The relationship of equation 3 shows that a higher spring constant and/or a higher elongation will result in a higher force "$F_E$".

Figure 18:
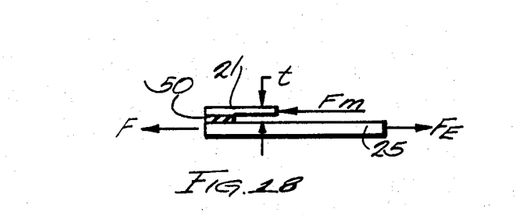

FIG. 18 is a free body diagram illustrating the forces on the composite structure at any phase. In FIG. 18, "F" is any external force applied to the elastic element, "$F_E$" is the force in the elastic element at any length, and "$F_m$" is the force applied to the outer cover through the bond points by the elastic element. To be in static equilibrium, the sum of the forces must be equal to zero, therefore:

$$F + F_m = F_E \tag{Eq. 4}$$

These forces vary in the three phases as follows:

(1) in phase 1, $F = F_T$, $F_m = 0$, and $F_E = F_T$.
(2) in phase 2, assuming the force $F_T$ is no longer applied to the elastic element, $F = 0$, and $F_m = F_E$.

(3) in phase 3, F, $F_m$ and $F_E$ are all effectively 0, disregarding any minor residual forces in the elements.

In order to reach phase 2, the beginning of buckling failure, the force "$F_E$" must be at least sufficiently large to generate force "$F_m$" equal to the critical load of the outer cover material; to reach phase 3, the force "$F_E$" must be greater than this critical load.

Figure 18A:
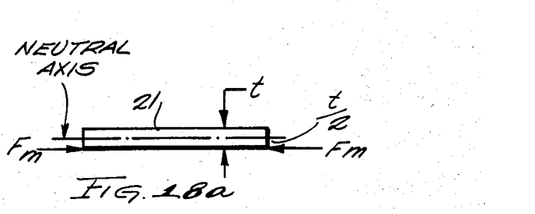

In phase 2, the outer cover material appears as an eccentrically loaded column with a compressive force $F_m$ located at a distance of $t/2$ from the neutral axis of the column, where "t" is the thickness of the outer cover material as shown in FIG. 18a. If we consider that $t/2$ is a very small value, we can approximate the column as one basically loaded at its neutral axis. The general equation for the critical load at which buckling occurs in this case can be found in *STANDARD Handbook for Mechanical Engineers*, Sixth Edition, page 5-54 as:

$$P_{cr} = \frac{n\pi^2 EI}{l^2} = \frac{n\pi^2 EA}{\left(\frac{l}{r}\right)^2} \qquad \text{(Eq. 5)}$$

Where:
- $P_{cr}$ = load at which the column buckles (fails);
- n = coefficient which depends on end support conditions;
- E = material modulus of elasticity;
- I = least moment of inertia of material cross section;
- A = cross sectional area of material;
- r = least radius of gyration of material;
- l = length of column between supports.

Figures 19, 20:
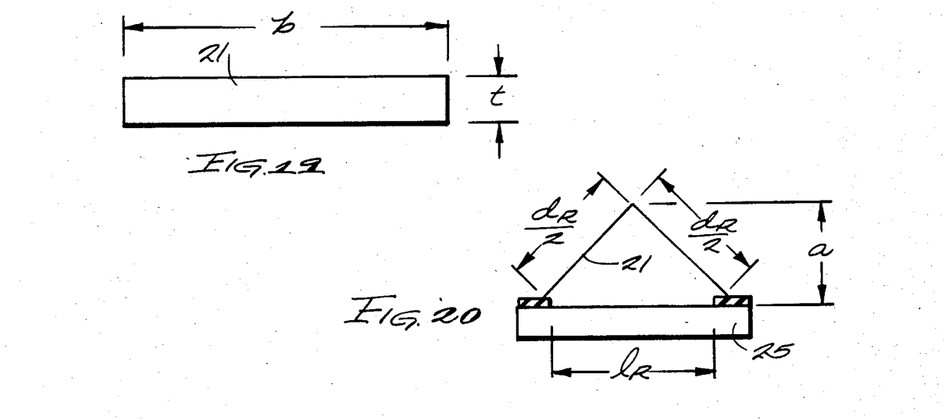

Considering a rectangular cross section of the material with thickness "t" and unit depth "b" as shown in FIG. 19 we have the following:

$$I = \frac{bt^3}{12}, A = tb, \text{ and } r^2 = \frac{I}{A} = \frac{t^3}{12}$$

(NOTE: To have buckling in the direction of the least radius of gyration, t is less than b.) Substituting these values into equation 5, the critical elastic force to cause the material to buckle is:

$$F_m = \left(\frac{n\pi^2 b}{12}\right)\left(\frac{t^3 E}{l^2}\right) \qquad \text{(Eq. 6)}$$

In any column, either concentrically or eccentrically loaded, that fails by buckling, a point in the loading is reached where the column failure is not dependent on the eccentricity of the load at all. At this point, the values are again only dependent on "E", "l" and "t". See *Mechanical Design and Systems Handbook*, 1964 McGraw-Hill, Inc., pages 15-32 to 15-34.

Substituting specific values into equation 6, we can determine the maximum force required to buckle a column of a specific material under a consistent end loading configuration as follows:

$$F_m = Q \frac{Et^3}{d_s^2} \qquad \text{(Eq. 7)}$$

In this equation, Q is a constant that includes the coefficient "n" for the end support conditions, depth of the material and numerical constants of integration. The value of Q can be determined empirically as has been done for specific cases, as in the Gorden-Rankins formula for structural main members with a ratio of l/r between 120 and 200. (See *Mechanical Design* reference above.)

From equation 7, it can be seen that for any given depth "b" of the column, the critical elastic force is directly proportional to the cube of the thickness "t" and the modulus of elasticity of the material "E" and inversely proportional to the square of the length of the column "$d_s$".

Figure 17:
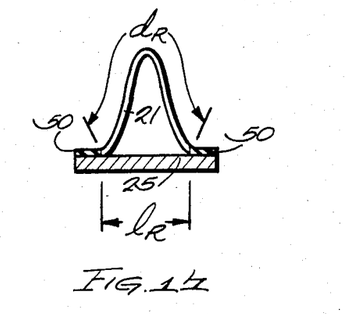

In FIG. 17, the unrestricted elastic element is shown in its retracted or unloaded length "$l_r$". The outer cover 21 is at length "$d_r$". At this point, the outer cover 21 is not supporting any loading from the elastic element and has not retracted. Therefore, $$d_r = d_s = l_s \qquad \text{(Eq. 8)}$$

An estimate of the height of the buckle may be made by assuming a triangular shape for the retracted layer 21. The amplitude "a" can be obtained from the Pythagorean Theorem using a right triangle with sides $l_r/2$, $d_r/2$ and the relationship of $l_s$ to $d_r$ as in equation 8:

$$\left(\frac{l_s}{2}\right)^2 = \left(\frac{l_r}{2}\right)^2 + a^2 \qquad \text{(Eq. 9)}$$

$$a = \frac{1}{2}\sqrt{l_s^2 - l_r^2} \qquad \text{(Eq. 10)}$$

Note that the amplitude can never be greater than $\frac{1}{2}$ the stretched length because for this to be true, the retracted length would have to be zero.

The stretched length of the elastic element can be referred to as a proportion of the original unstretched length. This proportion is the elongation "e" expressed in general terms of stretched length $L_s$ and retracted length $L_r$.

$$e = \frac{L_s - L_r}{L_r}, \text{ or } \% e = \frac{L_s - L_r}{L_r} \times 100 \qquad \text{(Eq. 11)}$$

Also:

$$L_s = L_r(e + 1) \qquad \text{(Eq. 12)}$$

$$L_r = \frac{L_s}{(e + 1)} \qquad \text{(Eq. 13)}$$

Substituting equation 13 into equation 10 using the specific lengths $l_s$ and $l_r$:

$$a = \frac{1}{2} l_s \sqrt{1 - \frac{1}{(e + 1)^2}} \qquad \text{(Eq. 14)}$$

Figure 21:
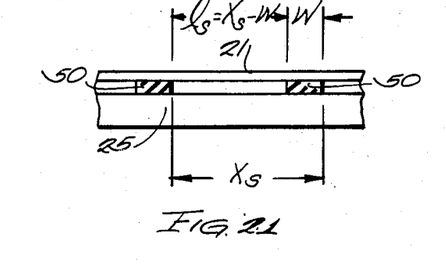
Figure 22:
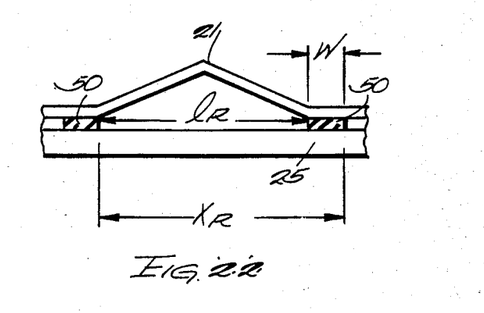

These values only consider the amount of the outer cover and elastic element composite between the bond points. To determine the total composite retraction, we must consider the amount of bonded area. FIGS. 21 and 22 show the distances including the length of the bond when the bond remains under tension in the retracted state. The following equations are based on FIGS. 21 and 22 and equation 13:

$$x_s = l_s + w = (x_s - w) + w \qquad \text{(Eq. 15)}$$

$$x_r = l_r + w = ((x_s - w)/(e + l)) + w \quad \text{(Eq. 16)}$$

The elongation "S" of the composite is now a ratio of $x_s$ to $x_r$ as follows:

$$S = \frac{X_s - X_r}{X_r}, \quad \text{(Eq. 17)}$$

which can be rewritten as $$S = \frac{e(X_s - w)}{X_s + we} \quad \text{(Eq. 18)}$$

Let the ratio of "w" to the total length "$x_s$" be defined as the ratio "Y" of the bonded area to the unbonded area.

$$Y = w/x_s \quad \text{(Eq. 19)}$$

Substituting this back into equation 18:

$$S = \frac{e(1 - Y)}{1 + Ye} \quad \text{(Eq. 20)}$$

Equation 20 shows that the elongation of the composite is only related to the initial elongation "e" of the elastic element and the ratio "Y" of the bonded area to the unbonded area.

It should be noted that the bond between the elastic element and the outer cover must be strong enough to maintain the force that is still over the bond points in phase 3. This force is, from equations 2 and 13:

$$F = \frac{K_E we}{e + 1} \quad \text{(Eq. 21)}$$

(d) Materials

A disposable garment having one or more elasticized body-encircling openings in accordance with this invention can be made of various materials suitable for the manufacturing techniques typically employed to produce such garments and appropriate to the end use intended for the garment. Garments such as disposable gowns, booties, caps may be made of a single layer of material (which can have two or more strata) whereas garments such as the disposable panty 10 described herein, infant diapers and adult incontinence garments may have several layers each selected for a specific functionality.

For example, the bodyside liner 20 or interior panel of the disposable panty 10 can be any flexible porous sheet which passes fluids therethrough to be absorbed in the absorbent batt 18, and other types of disposable garments may include a bodyside liner for the same purpose. The liner may comprise a nonwoven web or sheet of polyolefin fibers, such as polypropylene or polyethylene; a web of polyester fibers; a web of spun bonded polypropylene, polyethylene or polyester fibers; a web of rayon fibers; a bonded carded web of synthetic or natural fibers, and the like. The liner may also comprise a plastic film which is perforated to obtain the desired degree of moisture perviousness, or an expanded plastic webbing material or a scrim material. The liner preferably is made of a material which will feel soft and comfortable against the skin of an infant or adult.

An absorbent batt when included in a disposable garment, such as the absorbent batt 22 of the disposable panty 10, may comprise any suitable material capable of absorbing and retaining waste fluids that pass through the bodyside liner. The absorbent batt may comprise cellulosic material such as an air-formed batt of wood pulp fibers, commonly known as "fluff", which may include a heat fusible binder; a batt of melt blown fibers, such as of polypropylene, polyethylene, polyester and the like; a bonded carded web of synthetic or cellulosic fibrous materials; a composite of melt blown fibers of polypropylene, polyethylene, polyester or the like mixed with pulp fibers; or a blend of fluff with staple textile fibers such as rayon and the like. The batt may comprise one or more layers or combinations of the foregoing materials. In addition, the batt may include compounds added to increase its absorbency.

The exterior panel of a composite disposable garment, such as the outer cover 21 of the panty 10 and similar constructions, or the material of a single layer disposable garment such as a gown, bootie, cap, etc., can be of various types of materials including a plurality of closely-spaced bond points at least along the marginal portion(s) to which an elastic element is to be joined as described herein. The following types of materials are suitable for this purpose:

(1) Composite webs having an outer layer of nonwoven fibrous material and an inner layer of plastic material. Materials suitable for the outer layer (such as the layer 23 of the outer cover 21 of the panty 10) include a spun-bonded nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a spun-bonded nonwoven web of synthetic fibers such as polypropylene, polyethylene or polyester fibers mixed with cellulosic, pulp or textile fibers; or melt blown thermoplastic fibers, such as macrofibers or microfibers, of polypropylene, polyethylene, polyester or other thermoplastic materials or mixtures of such thermoplastic fibers with cellulosic, pulp or textile fibers. Suitable plastic materials for the inner layer (such as the inner layer 24 of the outer cover 21 of the panty 10) include polyolefin polymers such as polyethylene or polypropylene; polyolefin copolymers such as ethylene vinyl acetate, ethylene methyl acrylate or ethylene ethyl acrylate; polyvinyl chloride; or nylon. For many types of disposable garments, the inner layer is to provide a moisture barrier or liquid imperviousness. The plastic inner layer can be extrusion coated onto a web of the outer layer material, or the plastic inner layer may be a pre-formed web laminated to a web of the outer layer material such as by heat and pressure, sonic sealing, adhesive bonding etc. The bond points can be formed in a composite web by embossing with a suitable roll using heat and pressure as appropriate, or by other techniques capable of forming smooth fused bond points as previously described. The bond points may be located along the interior surface of the web or may be spaced slightly within the thickness of the web.

(2) Nonwoven webs of synthetic and/or natural fibers. Suitable materials include a spun-bonded nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a spun-bonded nonwoven web of synthetic fibers such as polypropylene, polyethylene or polyester fibers mixed with cellulosic, pulp or textile fibers; or melt blown thermoplastic fibers, such as macrofibers or microfibers, of polypropylene, polyethylene, polyester or other thermoplastic materials or mixtures of such thermoplastic fibers with cellulosic, pulp or textile fibers. The bond points can be formed in nonwoven webs of this type by the same techniques as described above in connection with composite webs.

(3) Plastic film, which may comprise single layer films of plastic material or multiple layer films of two or more similar or dissimilar plastic materials formed by lamination, extrusion coating or coextrusion of appropriate plastics. Suitable plastic materials include polyolefin polymers such as polyethylene or polypropylene; polyolefin copolymers such as ethylene vinyl acetate, ethylene methyl acrylate or ethylene ethyl acrylate; polyvinyl chloride; or nylon. The bond points can be formed in plastic films by embossing under heat and pressure with a roll having a suitable surface pattern or by extruding plastic films onto a chill roll having a patterned surface texture to form the bond points. The bond points should project slightly from the innermost surface of the film to which an elastic element is to be joined.

Any suitable elastomeric material can be employed for the elastic element in the practice of this invention that exhibits an elongation (defined as in Equation 11 above) at least in the range of 5% to 300%, preferably in the range of 25% to 200%. Also, the material of the elastic element should have a spring constant (K in equation 1, or $K_E$ in equation 2 of part (c) above) such that the elastic element can develop a force ($F_E$ in equation 3 of part (c) above) when elongated and joined to the garment large enough to result in buckling of the outer cover material between bond points when the elastic element retracts. However, the force developed by elongation of the elastic element when a garment is worn by a person should not be so high as to cause discomfort to the person or undue restriction of the part of a person's body in contact with the elasticized portion of the garment. We have found that material for the elastic element with a spring constant in the range of 10 to 30 gms/cm, preferably 15 to 22 gms/cm, is suitable for disposable garments such as infant's training pants constructed in accordance with the present invention. However, the spring constant can vary from these limits, depending upon the end use for a specific disposable garment. Various commercially available materials can be used, such as natural rubber, butyl rubber or other synthetic rubbers, urethane elastomeric material such as that available from B. F. Goodrich Company under the trademark TUFTANE, and elastomeric material available from the H. B. Fuller Company under the tradename FULLASTIC. The latter material (see e.g. U.S. Pat. No. 4,418,123) is based upon thermoplastic elastomeric copolymers of the A-B-A type such as those available from Shell Chemical under the trademark KRATON which have a rubbery midblock such as butadiene or isoprene and polystyrene end blocks, and is especially useful because it is a self-adhesive material and can be applied to the outer layer of a disposable garment without additional adhesive between the elastic element and the layers. The elastic element can be applied to the garment by any suitable means including adhesive bonding, heat sealing or sonic bonding, whichever is appropriate to the specific material selected for the elastic means.

(e) Physical Parameters

It is essential to the practice of the present invention that the outer layer or exterior panel of a disposable garment to which an elastic element is joined have several characteristics in order to obtain the micro-ribbing or micro-buckling condition described above.

As stated previously, at least the marginal portion of the outer layer is to have a plurality of closely-spaced bond points along its inner surface to which the elastic element is joined. There is to be a continuous array of the bond points along the entire marginal portion, which can be in either a regular or irregular pattern. Further, it is essential that each bond point has a specified area and is spaced from its neighboring bond points in the direction of elongation of the elastic means at a specified distance. The bond point area and spacing will, however, vary with the type of material employed for the exterior panel. The numerical ranges for these parameters of the exterior panel materials are as follows:

(1) For composite webs, as defined in part (d), each bond point should have an area in the range of 0.05 to 3 mm$^2$, preferably 0.09 to 0.56 mm$^2$ and most preferably 0.15 to 0.30 mm$^2$. The distance between bond points in the direction of elongation of the elastic element prior to joinder of the elastic element should be in the range of 0.5 to 4 mm, preferably 0.9 mm to 1.5 mm and most preferably 1.1 to 1.3 mm.

(2) For nonwoven webs, as defined in part (d), each bond point should have an area in the range of 0.05 to 3 mm$^2$, preferably 0.6 to 1.0 mm$^2$ and most preferably 0.7 to 0.85 mm$^2$. The distance between bond points in the direction of elongation of elastic element prior to joinder of the elastic element should be in the range of 0.25 to 4 mm, preferably 0.25 to 3 mm and most preferably 0.5 to 2 mm.

(3) For plastic films, as defined in part (d), each bond point should have an area in the range of 0.05 to 1.5 mm$^2$, preferably 0.1 to 0.5 mm$^2$ and most preferably in the range of 0.15 to 0.35 mm$^2$. The distance between bond points in the direction of elongation of the elastic element prior to joinder of the elastic element should be in the range of 0.05 to 2 mm, preferably 0.05 to 1 mm and most preferably 0.1 to 0.3 mm.

The bond points also should be spaced from one another transversely of the direction of elongation of the elastic element, but this spacing is not critical for the practice of the present invention and can vary within a wide range that may be less than or greater than the distance between bond points in the direction of elongation of the elastic element as stated above. However, the bond points are to be disposed along the entire interfacial contact area between the elastic element and the portion of the outer cover or external panel of the garment to which the elastic element is joined. Thus, with reference to FIGS. 4 and 7, for example, the bond points 50 are disposed along the entire area of the marginal portion of the outer cover 21 to which the first surface 26 of the elastic element 25 is joined. Considering the area of each bond point and the spacing between bond points in the direction of elongation of the elastic element within the essential ranges stated above, and bearing in mind that the bond points are to be spaced from one another transversely of the direction of elongation of the elastic element, the bond points should cover a specified percentage of the surface area of the marginal portion of the exterior panel to which the elastic element is joined; stated otherwise, the total area of the bond points should be a specified percentage of the area of the exterior surface (first surface 26) of the elastic element. Thus, the total area of the bond points should be as follows:

(1) For composite webs, as defined in part (d), the bond points should cover from 5 to 40%, preferably 5 to 30% and most preferably 8 to 15%, of the interfacial contact area between the elastic element and the marginal portion of the outer cover to which the element is joined.

(2) For nonwoven webs, as defined in part (d), the bond points should cover from 5 to 50%, preferably 8 to 30% and most preferably 11 to 20%, of the interfacial contact area between the elastic element and the marginal portion of the outer cover to which the element is joined.

(3) For plastic films, as defined in part (d), the bond points should cover from 20 to 80%, preferably 35 to 75% and most preferably 50 to 60%, of the interfacial contact area between the elastic element and the marginal portion of the outer cover to which the element is joined.

Secondly, the flexural rigidity of the material of the exterior panel is important. The construction of this invention is based upon an elastic element being joined to the bond points but not to the material between the bond points when in its retracted condition. In order for this structural relationship to be developed, it has been found that the flexural rigidity of the material should be within a specified range, measured in accordance with Federal Test Method Std. No. 191, depending on the material used for the exterior panel:

(1) For composite webs, as defined in part (d), the flexural rigidity should be in the range of 0.010 to 0.1 cm-g, preferably 0.02 to 0.08 cm-g and most preferably 0.03 cm-g to 0.055 cm-g.

(2) For nonwoven webs, as defined in part (d) the flexural rigidity should be in the range of 0.01 to 0.1 cm-g, preferably 0.02 to 0.08 cm-g and most preferably in the range of 0.03 to 0.055 cm-g.

(3) For plastic films, as defined in part (d), the flexural rigidity should be in the range of 0.002 to 0.008 cm-g, preferably 0.0025 to 0.0075 cm-g and most preferably 0.003 to 0.006 cm-g.

In addition, the formation of the micro-ribbing or striations of the exterior layer between the bond points upon retraction of the elastic element as described above involves mechanical control of folding the material between the bond points by the force developed with the elastic element. The thickness of the material affects the presence or absence of such folding or buckling and the degree of folding. The thickness of the material necessary to achieve this effect varies with the type of material used for the exterior layer, as follows:

(1) Composite webs, as defined in part (d), should be in the range of 0.0075 to 0.045 inches thick, preferably 0.009 to 0.020 inches thick, and most preferably 0.011 to 0.015 inches thick. These materials will generally have a basis weight in the range of 15 to 90 g/m$^2$, most often in the range of 30 to 55 g/m$^2$.

(2) Nonwoven webs, as defined in part (d), should be in the range of 0.005 to 0.03 inches thick, preferably 0.007 to 0.015 inches thick, and most preferably in the range of 0.009 to 0.013 inches thick. These materials will generally have a basis weight in the range of 10 to 50 g/m$^2$, most often in the range of 15 to 30 g/m$^2$.

(3) Plastic films, as defined in part (d), should be in the range of 0.0003 to 0.006 inches thick, preferably 0.0003 to 0.002 inches thick, most preferably in the range of 0.0005 to 0.001 inches thick.

To summarize, the (1) bond point area and spacing, (2) flexural rigidity, and (3) thickness of the exterior layer to which an elastic element is joined must be within the ranges stated above in order to produce an elasticized body-encircling opening in a disposable garment in accordance with the present invention and these characteristics are regarded as critical parameters for the practice of this invention.

As stated in part (a) of this description, another essential characteristic of the elasticized opening construction of the present invention is that the elastic element is joined to layers of the garment on both of its opposed surfaces. In the case of a composite garment such as the panty 10 described above, the first or exterior (relative to the manner in which the garment is worn) surface 26 of the elastic element 25 is joined to the outer cover 21 of the panty and the second or inner surface 27 thereof is joined to the bodyside liner 20 of the garment. In the case of a garment having a single exterior layer along the elasticized opening, such as illustrated in FIG. 6, the exterior and interior surfaces of the elastic element are joined to the same material which is folded over so as to have a portion on both sides of the elastic element. It is necessary to have a layer of material joined to the interior surface of the elastic element in order to equalize the stress on the elastic element from side to side of the element. If there is not a layer joined to the interior surface of the elastic element, the elastic element can curl transversely and thereby become longitudinally folded and/or can contract circumferentially and tend to ball up. This would have an adverse effect upon both the functionality of the elastic element and its appearance. It is considered preferable that the two layers of garment material joined to opposite surfaces of the elastic element have similar flexural rigidity. Also, it is preferred that the layer of material joined to the interior surface of the elastic element have a plurality of spaced bond points, but it is not necessary that the bond points of such layer have the same parameters as the bond points described above with respect to the layer of material joined to the exterior surface of the elastic element. Thus, there is a wider choice of the physical structure and mechanical properties of the layer joined to the interior surface of the elastic element as compared to the parameters described above with respect to the layer joined to the exterior surface thereof. The interior layer can be of the same types of materials suitable for the exterior layer as described previously in part (d) including composite webs, nonwoven webs and plastic films.

Figure 23:
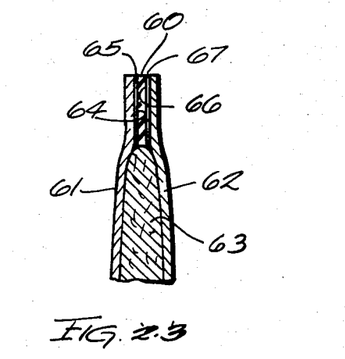
FIG. 23 is a sectional view of a disposable garment having a second form of elasticized opening of the present invention.
Figure 24:
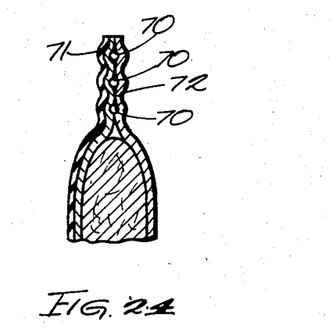
FIG. 24 is a sectional view of a disposable garment having a third form of elasticized opening of the present invention.

(f) Alternate Embodiments, FIGS. 23 and 24

As mentioned previously, the elastic element can be joined to a garment layer or layers by means of adhesive instead of being directly joined thereto as illustrated in FIGS. 1-10. This alternative is illustrated in FIG. 23. Elastic element 60 is joined between the outer cover 61 and bodyside liner 62 of a disposable garment having absorbent batt 63 between the two layers. The exterior surface 64 of the elastic element is joined to the outer cover along a thin layer of adhesive 65. The inner surface 66 of the elastic element is joined to the liner along a thin layer of adhesive 67. The adhesive layer 65 and 67 can be any adhesive, such as a liquid adhesive, hot melt adhesive, pressure sensitive adhesive, and the like, appropriate for bonding the material of the elastic element to material of the garment. Other structural features of the elasticized opening formed thereby remain as described previously, and the adhesive selected for this type of installation is to be joined only to the bond points of the two layers when the elastic element is retracted for the purposes of the present invention.

Also, however, joinder of the elastic element to a marginal portion of the outer cover with an adhesive layer, such as the adhesive layer 65 described above, enables an alternative construction for the bond points. The bond points 50 in FIGS. 1–21 are disclosed as being formed in the material of the outer cover 21 of the garment. However, when an elastic element is joined to a garment by means of an adhesive layer, it will be possible to form the bond points as part of the elastic element instead of as part of the outer cover material. Adhesive, such as the adhesive layer 65, can be screen printed onto the surface of an elastic element to be joined to the outer cover in a pattern comprising spaced discrete zones of adhesive that will form the bond points 50. When this alternative is employed, the zones of adhesive should have bond point area and spacing parameters within the ranges stated above in part (e). The surface of the elastic element to be joined to an inner liner can also be screen printed with discrete zones of adhesive which can have the same or different area and spacing.

The previous embodiments have shown the use of a single elastic element along the body-encircling portion to be elasticized. Also, the elastic elements in the embodiments previously described have been flat elastic tapes of rectangular cross-section including a pair of opposed planar surfaces. However, the present invention may be practiced with disposable garments having two or more elastic elements along a body-encircling portion and also with disposable garments including elastic elements having various cross-sectional configurations. FIG. 24 illustrates both of these alternatives. The section of a disposable garment shown therein includes a plurality of spaced elastic elements 70, each consisting of a filament or string of circular cross section, which construction is described and claimed in the application of Ales et al. entitled Disposable Garments with Multiple Strand Elasticized Openings, U.S. Ser. No. 690349, filed on the same date herewith and assigned to the assignee of this application, which is incorporated herein by reference. Each elastic element 70 is joined to the innermost surface of outer layer 71 of the garment and to the innermost surface of bodyside liner 72 of the disposable garment. One-half of the longitudinal circumferential surface of each element 70 is joined to the outer layer and the other half of the longitudinal circumferential surface of each elastic element is joined to the inner layer in this fashion. The outer edges of the layer 71, liner 72 and outermost elastic element 70 are substantially coincident. Again, the structural configuration of the innermost surface of the outer layer 71 and the manner in which each elastic element 70 is joined thereto are as described previously.

(g) Example

A disposable panty such as the panty 10 illustrated in FIG. 1 was constructed in a size suitable for use as an infant's training panty with an elasticized waistband as shown in FIG. 4 and elasticized legbands as shown in FIG. 24. The material of the outer cover, or exterior panel, of the disposable underpant was a two-layer composite web having an outer layer of nonwoven polypropylene fibers and an inner layer of ethylene methyl acrylate extrusion coated onto the nonwoven fibrous outer layer. The material of the outer cover, which is illustrated in the photomicrographs of FIGS. 11–14a, had the following physical parameters:

(1) Bond points measured as from about 0.15 to 0.30 $mm^2$ in area. (The bond points were formed along the entire area of the sheet material used for the outer cover as described previously in part (d)).

(2) Bond points along the waist and leg openings were spaced apart from about 1.1 to 1.3 mm in the direction of elongation of the elastic elements to be joined thereto. The bond points also were spaced transversely and covered about 8 to 15% of the surface area of the marginal portions of the outer cover joined to the exterior surface of the elastic elements.

(3) A flexural rigidity measured according to Federal Text Method STD. No. 191 of from about 0.030 to 0.055 cm-g; and (4) A thickness averaging from about 0.011 to 0.015 inches.

The panty had an interior panel comprising a bodyside liner of spun bonded polypropylene fibers having bond points in the same size pattern as the material of the outer cover. An absorbent batt of a composite of polypropylene microfibers and cellulosic fibers was sandwiched between the exterior panel and the interior panel. The elastic element along the waistband was a flat member about ¾ inch wide and 0.016 inches thick consisting of an A-B-A elastomeric copolymer (FULLASTIC) as described above in part (d) having a spring constant of 47 gms/cm. Three strands of the same elastomeric copolymer were arranged about each leg opening; the strands were each 1/16 inch in diameter and were spaced ¼ inch apart. The elastic element at the waist opening was stretched to about 84% and the elastic elements at the leg openings were stretched to about 117% and attached to the bond points of the exterior panel around these openings. The elastic elements were also joined to the interior panel along the leg and waist openings. Upon retraction of the elastic elements, the material of the exterior panel buckled between the bond points along the elastic elements at the waist and leg openings to form a continuous array of very fine striations or micro-ribbing between the bond points. This provided a disposable underpant garment with an attractive tailored appearance at the waist and leg openings. Tests of the garment with infants demonstrated that the underpant remained securely held in place about an infant's waist when the waist elastic was expanded as the garment was fit onto an infant and that the elasticized leg openings provided good sealing or gasketing against the leakage of fluids therethrough. Thus, a disposable underpant in accordance with this invention proved to be an attractive garment that was capable of providing the functionality required of a utilitarian disposable training pant.

There has thus been described a new construction for an elasticized marginal portion, generally a body-encircling opening, of a disposable garment. An elastic element is joined to two layers of a disposable garment along the marginal portion which is to be elasticized, and the elastic element can extend entirely or partially around the marginal portion. Further, the structure of the interface between the layers and the elastic element is to comprise a plurality of closely-spaced small bond points. The elastic element is joined to the bond points when in an extended or stretched condition, and when the elastic element is in a retracted condition the force generated thereby produces a micro-ribbing or micro-buckling of the exterior layer of the garment between the bond points. Other essential features necessary for obtaining the elasticized construction of this invention have been fully described hereinabove. The resulting elasticized structure achieved through the practice of this invention provides an exterior layer in a disposable garment which has a finely-ribbed or striated structure in the direction transverse to the direction of elongation of the elastic element. This produces a disposable garment having a tailored, pleasing appearance which closely resembles an elasticized portion heretofore previously achieved only with garments sewn of textile materials. In addition to the attractive appearance, however, an elasticized opening according to the present invention is extendable when a disposable garment is worn by a person so as to provide a snug, comfortable fit around the body portion which the elasticized margin encircles. This retains the garment in place in the desired position and also provides sealing against fluid leakage if such functionality is required with a specific type of disposable garment.

Various modifications of the specific embodiments of the present invention described hereinabove will suggest themselves to those of ordinary skill in the art and it is intended that all such modifications which employ the essential parameters of this invention as hereinafter claimed are to be encompassed within the scope of the appended claims.

We claim:

1. In a disposable garment including an outer marginal portion of material and an interior marginal portion of material along a part of said garment intended to fit around a portion of a wearer's body, and an elastic element joined thereto to provide an elasticized opening for said garment, the improvement wherein:
said elastic element includes an exterior surface disposed in mutually facing relationship with said outer marginal portion of material and an inner surface joined to said interior marginal portion of material, an outer edge portion of said elastic element, said outer marginal portion of material, and said interior marginal portion of material are substantially coincident, said outer marginal portion of material has a thickness in the range of about 0.0003 to about 0.03 inches, and a flexural rigidity in the range of about 0.002 to about 0.1 cm-g, and a plurality of bond points are uniformly disposed between and join together the mutually facing said elastic element exterior surface and said outer marginal portion of material, the area of each said bond point is between about 0.05 to about 3 mm$^2$, the distance between adjacent ones of said bond points in the direction of elongation of said elastic element prior to joining said elastic element to said outer marginal portion is between about 0.05 to about 4 mm, and the total area of said bond points is between about 5% to about 80% of the area of the mutually facing said exterior surface and said outer marginal portion, said elastic element is joined to said bond points when in an elongated condition and remains joined only to said bond points when in a retracted condition to provide an elasticized opening having micro-ribbing of said outer marginal portion of material between said bond points.

2. The garment of claim 1 wherein said bond points are integral with said outer marginal portion of material.

3. The garment of claim 1 wherein said elastic element outer edge portion, said outer marginal portion of material, and said interior marginal portion of material are coincident.

4. The garment of claim 1 wherein both said elastic element exterior surface and said elastic element inner surface are flat.

5. The garment of claim 1 wherein said elastic element has a circular cross-section and said exterior surface comprises one-half of a longitudinal circumferential surface of said elastic element, and said inner surface comprises a remaining longitudinal circumferential surface thereof.

6. The garment of claim 5 including a plurality of said elastic elements between said outer marginal portion of material and said interior marginal portion of material.

7. The garment of claim 1 wherein said outer marginal portion of material is a composite web having an outer layer of nonwoven fibrous material and an inner layer of plastic material, said outer marginal portion having a thickness in the range of about 0.0075 to about 0.045 inches and a flexural rigidity in the range of about 0.01 to about 0.1 cm-g, and wherein the area of each said bond point is between about 0.05 to about 3 mm$^2$, the distance between adjacent ones of said bond points is between about 0.5 to about 4 mm, and the total area of said bond points is between about 5% to about 40% of the area of the mutually facing said exterior surface and said outer marginal portion.

8. The garment of claim 1 wherein said outer marginal portion of material is a nonwoven web, said outer marginal portion having a thickness in the range of about 0.005 to about 0.03 inches and a flexural rigidity in the range of about 0.01 to about 0.1 cm-g, and wherein the area of each said bond point is between about 0.05 to about 3 mm$^2$, the distance between adjacent ones of said bond points is between about 0.25 to about 4 mm, and the total area of said bond points is between about 5% to about 50% of the area of the mutually facing said exterior surface and said outer marginal portion.

9. The garment of claim 1 wherein said outer marginal portion of material is a plastic film, said outer marginal portion having a thickness in the range of about 0.0003 to about 0.006 inches and a flexural rigidity in the range of about 0.002 to about 0.008 cm-g, and wherein the area of each said bond point is between about 0.05 to about 1.5 mm$^2$, the distance between adjacent ones of said bond points is between about 0.05 to about 2 mm and the total area of said bond points is between about 20% to about 80% of the area of the mutually facing said exterior surface and said outer marginal portion.

10. A method of elasticizing an opening of a disposable garment including an exterior panel with an outer marginal portion about the opening, an interior panel with an interior marginal portion about the opening, and an elastic element between the panels, wherein said elastic element includes an exterior surface disposed in mutally facing relationship with said outer marginal portion, comprising steps of:
- substantially coinciding an outer edge of the elastic element with the outer and the interior marginal portions,
- uniformly positioning a plurality of bond points between the outer marginal portion and the elastic element,
- while the elastic element is in an elongated state, adhering the elastic element, the bonds points, and the outer marginal portion together,
- microbuckling the outer marginal portion by relaxing the elastic element to its retracted state, and
- selecting controlling the microbuckling by selectively varying the area and spacing of the bond points so that the area of each said bond point is between about 0.05 to about 3 mm$^2$, the distance between adjacent ones of said bond points in the direction of elongation of said elastic element prior to joining said elastic element to said outer marginal portion is between about 0.05 to about 4 mm, and the total area of said bond points is between about 5% to about 80% of the area of the mutually facing said exterior surface and said outer marginal portion.

11. The method of claim 10 wherein the outer edge of the elastic element, the outer marginal portion, and the interior marginal portion are coincident.

12. The method of claim 10 wherein the plurality of bond points are integral with the outer marginal portion.

* * * * *